United States Patent [19]
Kruger

[11] Patent Number: 6,104,942
[45] Date of Patent: Aug. 15, 2000

[54] THERMOACOUSTIC TISSUE SCANNER

[75] Inventor: Robert A. Kruger, Indianapolis, Ind.

[73] Assignee: Optosonics, Inc., Indianapolis, Ind.

[21] Appl. No.: 09/076,385

[22] Filed: May 12, 1998

[51] Int. Cl.$^7$ ................................. A61B 8/00
[52] U.S. Cl. ........................... 600/407; 600/438
[58] Field of Search .................... 600/407, 473, 600/476, 437, 438; 601/3, 4; 606/2, 3; 73/587, 606; 367/7

[56] References Cited

U.S. PATENT DOCUMENTS

| | | | |
|---|---|---|---|
| 4,059,010 | 11/1977 | Sachs | 73/596 |
| 4,233,988 | 11/1980 | Dick et al. | 128/915 X |
| 4,246,784 | 1/1981 | Bowen | 178/736 |
| 4,255,971 | 3/1981 | Rosencwaig | 73/606 |
| 4,267,736 | 5/1981 | Quate | 73/606 |
| 4,385,634 | 5/1983 | Bowen | 128/653.1 |
| 4,481,821 | 11/1984 | Chamuel | 73/617 |
| 4,484,820 | 11/1984 | Rosencwaig | 374/6 |
| 4,681,120 | 7/1987 | Kunii | 178/915 X |
| 4,874,251 | 10/1989 | Thomas et al. | 374/45 |
| 4,950,897 | 8/1990 | Mandelis et al. | 250/334 |
| 5,070,733 | 12/1991 | Nagata et al. | 73/602 |
| 5,170,666 | 12/1992 | Larsen | 73/571 |
| 5,348,002 | 9/1994 | Caro | 128/664 X |
| 5,402,786 | 4/1995 | Drummond | 128/660.01 X |
| 5,615,675 | 4/1997 | O'Donnell et al. | 128/653.1 |
| 5,657,754 | 8/1997 | Rosencwaig | 128/633 |
| 5,713,356 | 2/1998 | Kruger | 128/653.1 |
| 5,840,023 | 11/1998 | Oraevsky et al. | 600/407 |

FOREIGN PATENT DOCUMENTS

| | | | |
|---|---|---|---|
| 0 018 771 | 4/1980 | European Pat. Off. | A61B 10/00 |
| 0 582 384 | 7/1992 | European Pat. Off. | G01N 21/17 |
| 3925312 | 4/1990 | Germany . | |
| 4446390 | 7/1996 | Germany . | |
| PCT 83/00009 | 1/1983 | WIPO | A61B 10/00 |
| WO97/27801 | 8/1997 | WIPO | A61B 8/13 |

OTHER PUBLICATIONS

Kruger, *Photo–acoustic ultrasound*, Med. Phys. 21(1): 127–131, 1994.

Kruger et al., *Photoacoustic ultrasound: pulse production and detection of 0.5% liposyn*, Med. Phys. 21(7): 1179–1184, 1994.

Kruger et al., *Photoacoustic Ultrasound: Theory and Experimental Results*, SPIE vol. 2134A: 114–121, 1994.

Nasoni et al., *Thermoacoustic Emission by Deeply Penetrating Microwave Radiation*, Poc. of IEEE Ultrasonic Symposium, 663–38, 1984.

Bowen et al., *Some Experimental Results of the Thermoacoustic Imaging of Tissue Equivalent Phantom Materials*, Proc. of IEEE Ultrasonic Symposium 2:823–27, 1981.

Bowen, *Radiation–Induced Thermoacoustic Soft Tissue Imaging*, Proc. of IEEE Ultrasonic Symposium 2: 817–822, Jun., 1981.

(List continued on next page.)

*Primary Examiner*—Marvin M. Lateef
*Assistant Examiner*—Shawna Shaw
*Attorney, Agent, or Firm*—Wood, Herron & Evans, L.L.P.

[57] ABSTRACT

Methods and apparatus for measuring and characterizing the localized electromagnetic wave absorption properties of biologic tissues in vivo, using incident electromagnetic waves to produce resultant acoustic waves. The tissue is exposed to modulating electromagnetic radiation, to produce modulating acoustic signals. The modulating acoustic signals are detected by an acoustic sensor which is primarily sensitive to acoustic radiation at a focal point distant from said sensor. Multiple measurements from multiple different focal points can then be combined into an image, or measurements at the same focal point at different excitation frequencies can be combined to produce an absorptivity spectrum for the tissue, either of which may be used for medical diagnostic purposes.

45 Claims, 2 Drawing Sheets

OTHER PUBLICATIONS

Hunter et al., *Acoustic signals of nonthermal origin from high energy protons in water,* J. Acoust. Soc. Am. 69(9), 1557–1562, Jun. 1981.

Bowen, *Acoustic Radiation Temperature of Non–Invasive Thermometry,* Automedica, vol. 8, 247–267, 1987.

Hebden et al., *Tomographic Imaging Using Picosecond Pulses of Light,* SPIE vol. 1443, Medical Imaging V: Image Physics 294–300, 1991.

Beard et al., *Characterization of post mortem arterial tissue using time–resolved photoacoustic spectrosopy at 436, 461 and 532 nm,* Phys. Med. Biol. 42 (1997) 177–198.

Shan et al., *Modeling of a photoacoustic probe designed for medical applications,* Ultrasonics 34 (1996) 575–577.

Ossoff et al., *Computer–Assisted Surgical Techniques: A Vision for a Future of Otolaryngology—Head and Neck Surgery,* Jrnl of Otolaryngology, vol. 23, No. 5 (1994) 354–359.

Chen et al., *A new laser–ultrasound transducer for medical applications,* Ultrasonics vol. 32, No. 4 (1994) 309–313.

Appledorn et al., *Energy Deposition Patterns in the Breast at 1064 nm for Photoacoustic Ultrasound,* SPIE vol. 2708 (1996) 655–664.

Fang et al., *Microwave Applicators for Photoacoustic Ultrasonography,* SPIE vol. 2708 (1996) 645–654.

Kruger et al., *Photoacoustic ultrasound (PAUS)—Reconstruction tomography.,* Med. Phys. 22 (10), Oct. 1995, pp. 1605–1609.

Liu et al., *Simulation of Photoacoustic Signal Production in Human Breast Phantoms at 1064 nm,* SPIE vol. 2708, 1996, pp. 312–322.

THERMOACOUSTIC TISSUE SCANNER

CROSS REFERENCE TO RELATED APPLICATIONS

This application is related to earlier-filed U.S. patent application Ser. No. 08/719,736, now U.S. Pat. No. 5,713,356, filed by the same inventor as the present application, and assigned to the same assignee as the present application, which is incorporated by reference herein in its entirety.

FIELD OF THE INVENTION

The present invention relates to imaging properties of tissue based upon differential absorption of electromagnetic waves in differing tissue types by photo-acoustic techniques.

BACKGROUND OF THE INVENTION

It is well established that different biologic tissues display significantly different interactions with electromagnetic radiation from the visible and infrared into the microwave region of the electromagnetic spectrum. While researchers have successfully quantified these interactions in vitro, they have met with only limited success when attempting to localize sites of optical interactions in vivo. Consequently, in vivo imaging of disease at these energies has not developed into a clinically significant diagnostic tool.

In the visible and near-infrared regions of the electromagnetic spectrum, ubiquitous scattering of light presents the greatest obstacle to imaging. In these regions, scattering coefficients of $10-100$ mm$^{-1}$ are encountered. Consequently, useful numbers of unscattered photons do not pass through more than a few millimeters of tissue, and image reconstruction must rely on multiply-scattered photons. While efforts persist to use visible and infrared radiation for imaging through thick tissue (thicker than a few centimeters), clinically viable imaging instrumentation has not been forthcoming.

In the microwave region (100–3000 MHZ), the situation is different. Scattering is not as important, since the wavelength (in biologic tissue) at these frequencies is much greater than the "typical" dimension of tissue inhomogeneities ($\approx 1$ $\mu$m). However, the offsetting effects of diffraction and absorption have forced the use of long wavelengths, limiting the spatial resolution that can be achieved in biologic systems. At the low end of the microwave frequency range, tissue penetration is good, but the wavelengths are large. At the high end of this range, where wavelengths are shorter, tissue penetration is poor. To achieve sufficient energy transmission, microwave wavelengths of roughly 2–12 cm (in tissue) have been used. However, at such a long wavelength, the spatial resolution that can be achieved is no better than roughly ½ the microwave length, or about 1–6 cm.

In vivo imaging has also been performed using ultrasound techniques. In this technique, an acoustic rather than electromagnetic wave propagates through the tissue, reflecting from tissue boundary regions where there are changes in acoustic impedance. Typically, a piezoelectric ceramic chip is electrically pulsed, causing the chip to mechanically oscillate at a frequency of a few megahertz. The vibrating chip is placed in contact with tissue, generating a narrow beam of acoustic waves in the tissue. Reflections of this wave cause the chip to vibrate, which vibrations are converted to detectable electrical energy, which is recorded.

The duration in time between the original pulse and its reflection is roughly proportional to the distance from the piezoelectric chip to the tissue discontinuity. Furthermore, since the ultrasonic energy is emitted in a narrow beam, the recorded echoes identify features only along a narrow strip in the tissue. Thus, by varying the direction of the ultrasonic pulse propagation, multi-dimensional images can be assembled a line at a time, each line representing the variation of acoustic properties of tissue along the direction of propagation of one ultrasonic pulse.

For most diagnostic applications, ultrasonic techniques can localize tissue discontinuities to within about a millimeter. Thus, ultrasound techniques are capable of higher spatial resolution than microwave imaging.

The photoacoustic effect was first described in 1881 by Alexander Graham Bell and others, who studied the acoustic signals that were produced whenever a gas in an enclosed cell is illuminated with a periodically modulated light source. When the light source is modulated at an audio frequency, the periodic heating and cooling of the gas sample produced an acoustic signal in the audible range that could be detected with a microphone. Since that time, the photoacoustic effect has been studied extensively and used mainly for spectroscopic analysis of gases, liquid and solid samples.

It was first suggested that photoacoustics, also known as thermoacoustics, could be used to interrogate living tissue in 1981, but no subsequent imaging techniques were developed. The state of prior art of imaging of soft tissues using photoacoustic, or thermoacoustic, interactions is best summarized in Bowen U.S. Pat. No. 4,385,634. In this document, Bowen teaches that ultrasonic signals can be induced in soft tissue whenever pulsed radiation is absorbed within the tissue, and that these ultrasonic signals can be detected by a transducer placed outside the body. Bowen derives a relationship (Bowen's equation 21) between the pressure signals $p(z,t)$ induced by the photoacoustic interaction and the first time derivative of a heating function, $H(z,t)$, that represents the local heating produced by radiation absorption. Bowen teaches that the distance between a site of radiation absorption within soft tissue is related to the time delay between the time when the radiation was absorbed and when the acoustic wave was detected.

Bowen discusses producing "images" indicating the composition of a structure, and detecting pressure signals at multiple locations, but the geometry and distribution of multiple transducers, the means for coupling these transducers to the soft tissue, and their geometrical relationship to the source of radiation, are not described. Additionally, nowhere does Bowen teach how the measured pressure signals from these multiple locations are to be processed in order to form a 2- or 3-dimensional image of the internal structures of the soft tissue. The only examples presented are 1-dimensional in nature, and merely illustrate the simple relationship between delay time and distance from transducer to absorption site.

The above-referenced U.S. Patent filed by the present inventor, details a diagnostic imaging technique in which pulses of electromagnetic radiation are used to excite a relatively large volume of tissue and stimulate acoustic energy. Typically, a large number of such pulses (e.g., 100 to 100,000), spaced at a repetition interval, are generated to stimulate the tissue The above-referenced patent application discloses detailed methods for measuring the relative time delays of the acoustic waves generated by a sequence of such pulses, and for converting these time delays into a diagnostic image.

SUMMARY OF THE INVENTION

The present invention improves upon what is disclosed by Bowen and in the above-referenced U.S. Patent Application in several ways. First, the present invention uses continuous, periodically modulated radiation in place of narrowly pulsed radiation. Continuous radiation can be used to stimulate sonic waves continuously without having to wait for sequences of pulses. The localizing method for reconstructing uses constructive and destructive interference of periodic sonic waves generated by the continuous radiation. This approach can substantially increase the signal-to-noise ratio of the recorded signal, reduce the power requirements of the radiation source, and simplify the reconstruction methodology and the complexity of the associated apparatus.

Specifically, in one embodiment, the invention features a method of imaging tissue structures from localized absorption of electromagnetic waves, by irradiating the tissue with continuously modulating electromagnetic radiation, and detecting the resulting acoustic waves with an acoustic sensor which is primarily sensitive to acoustic radiation at a first focal point distant from the sensor. The sensor is used to collect data from two or more different locations in the tissue, and this data is combined to produce an image of structures in the tissue.

In a second embodiment, a similar apparatus is used in characterizing tissue at a focal point of the acoustic sensor. In this embodiment, continuous, frequency modulating electromagnetic radiation is generated by the source, and the resultant pressure waveforms arriving at the acoustic sensor from the focal point, are compared to the frequency of the electromagnetic radiation, to form a measure of the absorptivity spectrum of tissue located at the focal point of the acoustic sensor.

The above and other objects and advantages of the present invention shall be made apparent from the accompanying drawings and the description thereof

BRIEF DESCRIPTION OF THE DRAWING

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF SPECIFIC EMBODIMENTS

Figure 1:
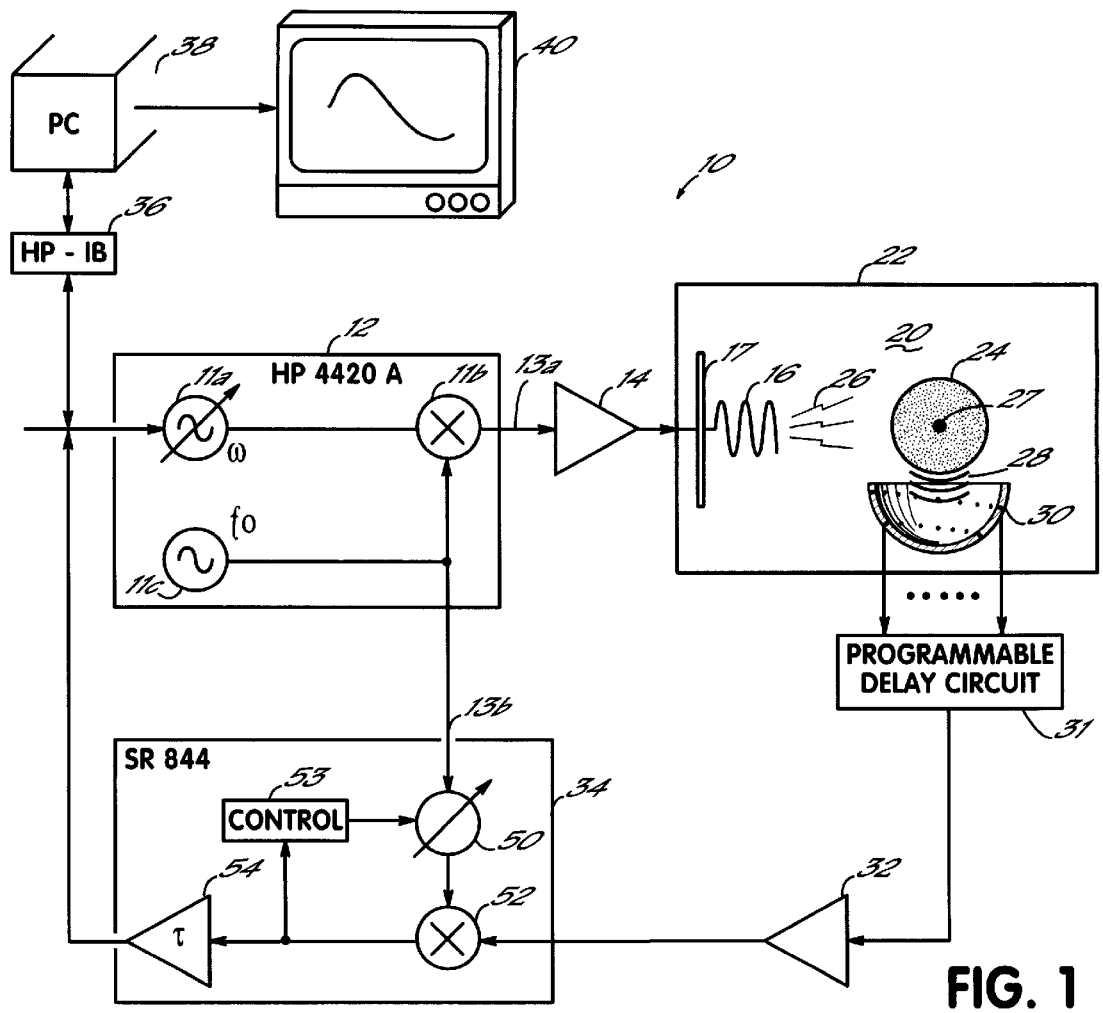
FIG. 1 is a functional block diagram of a photoacoustic scanner for scanning tissue in accordance with a first embodiment of the present invention.

FIG. 1 illustrates a photoacoustic scanner 10 in accordance with one embodiment of the present invention, which displays several key elements for successful photoacoustic scanning of tissue.

The instrumentation 10 used in this embodiment is shown schematically in FIG. 1. The instrumentation comprises an RF signal generator 12 (e.g., a Hewlett Packard signal generator, Model 4420A), including a carrier frequency generator 11a operating at a frequency $\omega$, whose amplitude will be modulated periodically by a modulator 1 lb in response to a modulating signal at a much lower frequency $f_0, f_0 << \omega$ generated by a source 11c. The modulation may be sinusoidal, square wave, or any other shape. For the remainder of this discussion, sinusoidal modulation will be assumed. Signal generator 12 produces an output on line 13a comprising the modulated RF signal, and an output on line 13b comprising the baseband modulating signal at frequency $f_0$.

Signal generator 12 is controlled via digital signals received at an HP-IB digital interface 36, to programmably generate a desired carrier frequency $\omega$ and modulating signal at frequency $f_0$. The modulated RF signal output by modulator 11b on line 13a is amplified by a broadband amplifier 14 (e.g., from Amplifier Research, rated at 100 W), which will drive a broadband, water-immersed antenna 16, which is positioned opposite to a ground plane 17 to direct radiation into water or another acoustic coupling media 20 in a tank 22. The tissue sample 24 to be scanned is also immersed in tank 22. RF energy generated by antenna 16 will irradiate the tissue sample continuously with RF energy as shown at 26. Periodic energy absorption within the tissue sample will stimulate acoustic waves that will propagate isotropically within the imaging tank as shown at 28.

In one embodiment, the imaging tank 22 is filled with deionized and distilled (DD) water 20. The DD water is an efficient coupling medium for the acoustic waves between the sample 24 and the transducer and also provides good microwave energy coupling between the antenna 16 and the sample 24. In addition, DD water has high permittivity ($\epsilon_r = 77$), which reduces the wavelength of the microwaves by a factor of 8.8 as compared to free space, which allows a similar reduction in the size of antenna 16.

A focused transducer 30, whose focus point 27 lies within the tissue sample 24, will detect the continuously emitted sound waves 28 from the tissue. The frequency response of transducer 24 is chosen to be primarily sensitive to sound waves that are at or near the modulation frequency $f_0$. In an embodiment of the present invention suitable for two- or three-dimensional imaging of tissue as well as generation of absorptivity spectra, the focused transducer has a spherical surface, carrying an array of evenly spaced small transducers. (A spherical-surface transducer array can be seen in FIG. 8 of the above-referenced U.S. Pat. No. 5,713,356, which is incorporated herein by reference.) The outputs of the individual transducers are fed to a programmable delay circuit 31, for introducing relative programmable delays to those signals and then producing an output delivered to amplifier 32 which is proportional to the sum of the delayed transducer signals. By programmably altering the transducer delays under control of computer 38 via HP-IB bus 36 or another suitable control mechanism, the focus point of the transducer 30 can be moved to desired positions in the tissue 27.

The operation of the programmable delay circuit 31 is as follows. Define R to be the radius of curvature of the surface of the transducer array, and $\sigma_i(t)$ to be the output of transducer i at time t. If the outputs of all transducers are summed together by programmable delay circuit 31 without introducing any delays, then the output of the programmable delay circuit 31 will be a signal $$\sigma(t) = \sum_{i=1}^{N} \sigma_i(t).$$

Due to constructive interference, this signal will be primarily sensitive to signals originating from a sensitive volume around the center of curvature of the surface of the transducer array (see the discussion of FIG. 2, below).

To vary the position of the sensitive volume, the programmable delay circuit 31 utilizes programmable delay circuits to introduce a delay into each of the signals $\sigma_i(t)$ output from the transducers of the transducer array. Mathematically, $$\sigma_j(t) \equiv \sum_{i=1}^{N} \sigma_i(t - \delta_{ij}),$$

where $\vec{r}_i$=position of the i-th transducer, $\vec{r}_j$=S the position of the point in space to be "focused" upon, and $\delta_{ij}$=the time delay for the i-th transducer for the spatial location j. This time delay is calculated as $$\delta_{ij} = \text{mod}\left(\frac{|\vec{r}_i - \vec{r}_j| - R}{v_s}, \frac{1}{f_0}\right),$$

where $f_0$ is the frequency of the baseband modulating signal, $1/f_0$ is the temporal "period" associated with this frequency, and the function "mod(a,b)" is defined as the remainder after dividing "a" by "b."

In an alternative embodiment, a focused transducer with a fixed focus point may also be used, for example to generate an absorptivity spectrum for the tissue at a single point 27, or to generate an image by mechanically moving the transducer and thereby moving its focus point. A fixed focus point transducer can be obtained from Panametrics., Inc. of Waltham, Mass. This focused transducer has the property that only sound waves that originate at or near the focal point of the transducer strike all regions of the transducer's front surface simultaneously, thus producing constructive interference. Where such a transducer is used, the output of the transducer is directly connected to amplifier 32.

Signals from programmable delay circuit 31 or from a fixed focused transducer are amplified by a narrow band amplifier 32, having a primary amplification band at or near modulation frequency $f_0$. The output of amplifier 32 is connected to an RF lock-in amplifier 34 (e.g., from Stanford Research, SR844). A second input to lock-in amplifier 34 is connected to the baseband modulating signal at frequency $f_0$ on line 13b. Lock-in amplifier 34 phase locks the signal output from amplifier 32 with the modulating signal on line 13b, using phase-sensitive detection. The phase locked output from amplifier 32 is then passed through a low-pass filter 54 (time constant=$\tau$). The resulting DC output from the lock-in amplifier 34 is proportional to the microwave absorption properties of the sample in the sensitive volume.

In use, the focus point of transducer 30 may be scanned about the inside of the tissue sample 24, while collecting signal amplitude data from amplifier 34. The amplitude data can then be plotted as a grey-scale as a function of focal point position to form a two- or three-dimensional image of the tissue structures. Alternatively, if the microwave frequency is swept slowly (compared to $\tau$) over time across some range of values while the focal point is maintained, an absorption spectrum for the tissue at the focal point of the transducer will be generated over time. This spectrum can be displayed by PC 38 on display terminal 40 and used to characterize the tissue at the focal point. These techniques can be combined to generate two- or three-dimensional images reflecting absorptivity spectra at multiple focal points.

A brief discussion of the operating theory of the instrumentation 10 is now in order. The stimulating microwave radiation at frequency $\omega$ propagates through the entire volume of tissue 24 virtually instantaneously (at the speed of light) creating local stimulating power $I(\omega,x,y,z,t)=I_0(\omega,x,y,z)(1+\sin(2\pi f_0 t))$, where $I_0(\omega,x,y,z)$ is the peak power of the stimulating radiation that reaches position (x,y,z) within the tissue and $\sin(2\pi f_0 t)$ is the modulating signal. In response to this stimulating radiation, pressure signals p(107,x,y,z) are produced that are proportional to the first time-derivative of the local stimulating power:

EQ. 1

$$p(\omega, x, y, z) =$$

$$A\mu(\omega, x, y, z)\frac{\partial I(\omega, x, y, z)}{\partial t} = 2\pi f_0 A\mu(\omega, x, y, z)I_0(\omega, x, y, z)\cos(2\pi f_0 t)$$

where A is a constant and $\mu(\omega,x,y,z)$ is the local energy-absorption coefficient at the stimulating radiation frequency $\omega$.

For the sake of discussion, assume the surface of the transducer has a focal point at the origin (0, 0, 0). Further assume the pressure wave originating within a volume element surrounding the focal point of the transducer will produce constructive interference. For this reason we can calculate the component of the output of the transducer $\sigma(\omega, 0, 0, 0, t)$ due to energy-absorption at its focal point, provided the stimulating radiation persists for a time t>R/$v_s$ where $v_s$ is the velocity of sound in the tissue 24 and coupling media 20. The component of the transducer output due to energy absorption at is focal point can therefore be written:

$$\sigma(\omega, 0,0,0,t) = 2\pi f_0 - AS\mu(\omega,0,0,0)I_0(\omega,0,0,0)\cos(2\pi f_0(t-R/v_s))dV \quad Q. \ 2$$

where S is the sensitivity of the transducer (output voltage/input pressure originating at focal point) and dV is the volume element associated with the focal point.

In general, pressure waves that originate from regions other than the focal point will arrive out of phase. Due to this temporal dispersion, destructive, as well as constructive interference is produced at the transducer surface. To characterize this behavior, we will model the transducer as a spherical surface of radius $R_1$, with center at the origin. This is an accurate model for a fixed focal point transducer such as is available from Panametrics as well as the multi-element transducer 30 of FIG. 1, when combined with a suitably programmed delay circuit 31 causing the focal point of transducer 30 to be at the origin. In this more general case we can write:

$$\sigma(\omega, x, y, z, t) \approx 2\pi f_0 AS\mu(\omega, x, y, z)I_0(\omega, x, y,$$

$$z)dV\frac{1}{4\pi R^2}\int_0^\pi \cos\left(2\pi f_0\left(t - \frac{R}{v_s} + \frac{r}{v_s}\cos\Phi\right)\right)2\pi R^2 \sin\Phi d\phi$$

$$\sigma(\omega, x, y, z, t) \approx 2\pi f_0 AS\mu(\omega, x, y, z)I_0(\omega, x, y,$$

-continued $$z)dV\cos(2\pi f_0(t - R/v_s))\frac{\sin(2\pi f_0 r/v_s)}{2\pi f_0 r/v_s}$$

Figure 2:
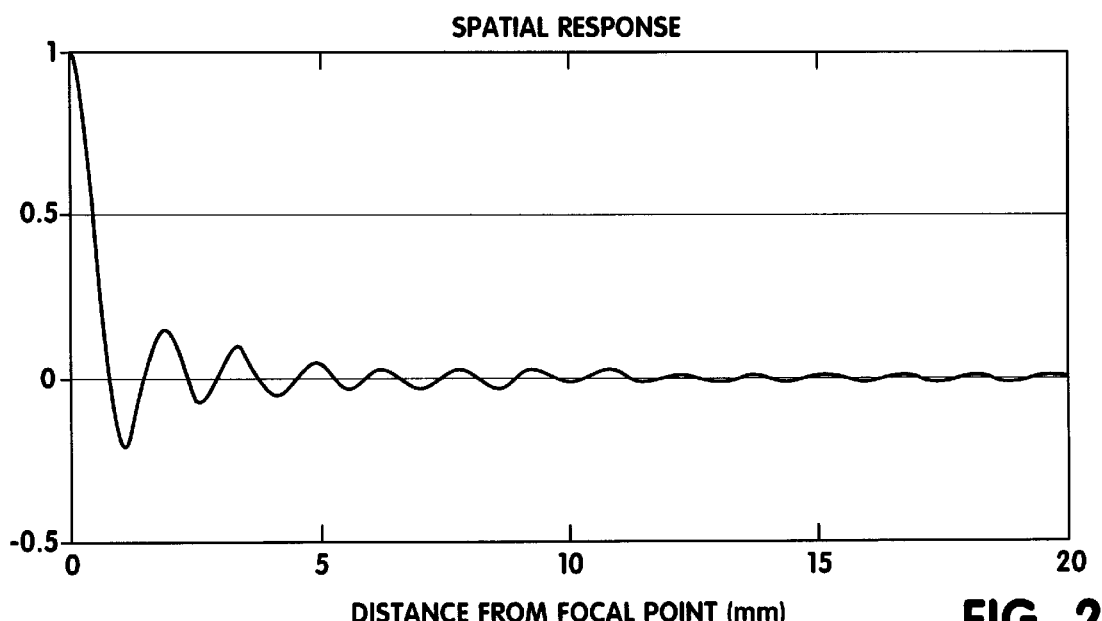
FIG. 2 is plot of the spatial response of a spherical transducer surface as a function of the distance of the acoustic source from the focal point of the spherical transducer.

EQ. 3
where $r \equiv /(x,y,z)/$. From Eq. 3 it is evident that only pressure waves of frequency $f_0$ are produced within the tissue volume, and because of the term $$\frac{\sin(2\pi f_0 r/v_s)}{2\pi f_0 r/v_s}$$

the strongest contribution to the signal detected by the transducer is due to acoustic waves originating near the focal point. The term $$\frac{\sin(2\pi f_0 r/v_s)}{2\pi f_0 r/v_s}$$

is plotted with respect to r in FIG. 2 for $f_0 = 1.0$ MHZ.
The function $$\frac{\sin(2\pi f_0 r/v_s)}{2\pi f_0 r/v_s}$$

crosses zero the first time at $r = r_0 = v_s/2f_0$. This radius defines the sensitive volume surrounding the focal point that contributes most to the signal received by the transducer. The total detected signal associated with this sensitive volume is given by:
EQ. 4

$$\sigma(|r| < r_0, t) \approx 8\pi^2 f_0 AS\langle\mu(\omega, x, y, z)\rangle_{r_0}\langle I_0(\omega, x, y,$$

$$z)\rangle_{r_0}\cos(2\pi f_0(t - R/v_s))\int_0^{v_s/2f_0}\frac{\sin(2\pi f_0 r/v_s)}{2\pi f_0 r/v_s}r^2 dr,$$

$$\sigma(|r| < r_0, t) \approx \frac{v_s^3}{f_0^2}AS\langle\mu(\omega, x, y, z)\rangle_{r_0}\langle I_0(\omega, x, y, z)\rangle_{r_0}\cos(2\pi f_0(t - R/v_s))$$

where $r \equiv |(x,y,z,)|$, $4\pi r^2 dr = dV$, and $\langle (I_0(\omega,x,y,z)\rangle_{r_0}$ is the mean radiation intensity and $\langle\mu(\omega,x,y,z)\rangle_{r_0}$ is the mean energy-absorption coefficient within the sensitive volume, $|r| < r_0$.

Referring again to FIG. 1, details of the phase tracking performed by lock-in amplifier 34 can be explored. As noted above, the transducer output is amplified by a narrow-band amplifier 32, with center frequency $f_0$. The output of the narrow-band amplifier 32 is sent to a lock-in amplifier 34, where it is mixed with the original, radiation-modulating signal from source 11c in signal generator 12. A phase adjustment circuit 50 within lock-in amplifier 34 allows the phase of the modulating signal to be varied. The phase-adjusted output of circuit 50 is coupled to a demodulating amplifier 52. Demodulating amplifier 52 produces an output which is the product of the signals delivered at its two inputs. The output of the demodulating amplifier 52 $\Phi(t)$ can be written as:
EQ. 5

$$\Phi(t) = \frac{v_s^3}{f_0^2}AS\langle\mu(\omega, x, y,$$

-continued $$z)\rangle_{r_0}\langle I_0(\omega, x, y, z)\rangle_{r_0}\cos(2\pi f_0(t - R/v_s))\cos(2\pi f_0(t - \theta))$$

Where $\theta$ represents the adjustable phase of the reference signal controlled by phase adjustment circuit 50. Control circuit 53 adjusts the phase angle $\theta$ to maximize the amplitude of the output of demodulating amplifier 52. This means that $\theta$ will be adjusted to the value $\theta = R/V_s$. If $\theta$ is adjusted so that $\theta = R/v_s$, $\Phi(t)$ becomes:
EQ. 6

$$\Phi(t) = \frac{v_s^3}{f_0^2}AS\langle\mu(\omega, x, y, z)\rangle_{r_0}\langle I_0(\omega, x, y, z)\rangle_{r_0}\frac{1}{2}(1 + \cos(4\pi f_0(t - R/v_s)))$$

which is the sum of a constant term and sinusoidal term of frequency $2f_0$.

The output of demodulating amplifier 52 is fed to a low-pass filter 54, whose time constant r is chosen to be much greater than $1/f_0$. With this choice of time constant the output of the low-pass filter 54 isolates the constant term in Eq. 6, $$\frac{v_s^3}{2f_0^2}AS\langle\mu(\omega, x, y, z)\rangle_{r_0}\langle I_0(\omega, w, y, z)\rangle_{r_0},$$

which is proportional to the mean energy-absorption coefficient near the focal region of the transducer. This is an important feature of this thermoacoustic localization methodology.

Since the effective bandwidth of the detection circuitry 50, 52, 53 is determined by the time constant of the low-pass filter 54, extremely low bandwidth circuitry can be used in control circuit 53, adjustment circuit 50 and demodulating amplifier 52 while remaining primarily sensitive to the modulation frequency $f_0$ of the radiation source. The net result is a dramatic decrease in the detector's electronic noise compared to the wide-bandwidth detector required with pulsed acquisition devices such as that disclosed in the above-referenced U.S. Patent. For these devices the bandwidth of the detection system is on the order of $2f_0$, where $f_0$ is the center frequency of the transducer. Assuming that the time constant of the low-pass filter is 1 second, the electronic noise will be reduced by a factor of $\sqrt{2f_0}$ or 1400 for $f_0 = 1$ MHz compared to a pulsed acquisition system. This is an important property of the thermoacoustic localization methodology of the present invention.

As described so far, the thermoacoustic apparatus can measure a quantity proportional to the mean energy-absorption coefficient of the tissue in the vicinity of the focal point of the transducer at the frequency (energy) of the stimulating radiation. If the frequency $\omega$ of the radiation source is changed, the energy absorption coefficient will change as will. In general, the way in which $\mu(\omega,x,y,z)$ various as $\omega$ changes is determined by the type of tissue(s) present within the sensitive volume. If $\mu(\omega,x,y,z)$ can be measured over some range of $\omega$, it is possible to infer what type of tissue is present within the sensitive volume. Making such a measurement is the goal of spectroscopy.

The apparatus illustrated in FIG. 1 is shown acquiring volume-localized, spectroscopic information from the focal point 27 in tissue 24. In this embodiment, PC 38 causes the operating frequency $\omega$ of the radiation source 11a to be swept over some range of frequencies $\omega_1 \rightarrow \omega_2$ during some time period $\Delta T$ For the sake of exposition it is assumed that the intensity of the radiation is maintained constant as $\omega$ is varied.) If the time period $\Delta T$ is made long compared to the time constant of the low-pass filter, i.e., $\Delta T \gg \tau \gg 1/f_0$, the output of the low-pass filter will vary in proportion to $<\mu(\omega,x,y,z)<_{r_0}$. A graphical display of $\mu(\omega,x,y,z)$ is formed on display 40 by plotting $\omega$ along the x (horizontal) axis and the output of the low-pass filter 54 of lock-in amplifier 34 along the y (vertical) axis. This plot is a visual representation of the spectrum of $\mu(\omega,x,y,z)$ over the range $\omega_1 \to \omega_2$ and is illustrated in FIG. 1.

There are several ways in which the stimulating radiation and the transducer can be coupled to the tissue being examined. Examples are given in FIGS. 3–6 below.

Figure 3:
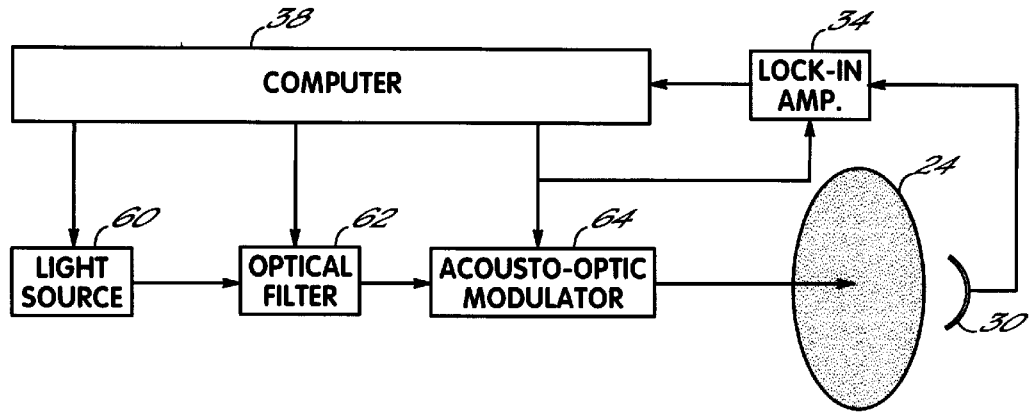
FIG. 3 illustrates a first alternative embodiment of an apparatus for coupling stimulating radiation to tissue and collecting acoustic signals therefrom.

In FIG. 3, the EM radiation is provided by a light source (ultraviolet, visible or infrared), such as a single-frequency laser, or a broadband lamp 60 (such as a halogen lamp), which produces a continuum of frequencies over some predetermined range. If the light source is broadband, the frequency of the light that passes on to the tissue can be narrowed and varied using an optical filter 62. The optical filter 12 only allows a narrow range of light frequencies to pass through. By either changing the filter material or rotating it to a new position, the light frequency that passes on to the tissue can be controlled. If the light source 60 is a laser, the optical filter 62 is not needed. In this case the operating frequency of the laser can be adjusted electronically. The intensity of the light beam can be modulated by a device called an acousto-optic modulator 64, which is a standard device for controlling light intensity. In FIG. 3, the transducer 30 is placed in contact with the tissue 24 over a region different from where the modulated light beam enters. A computer 38 controls operation of the light source 60, optical filter 62 and acousto-optical modulator 64. It also gathers data from transducer 30 via a lock-in amplifier 34 for processing according to the methodology described previously.

Figure 4:
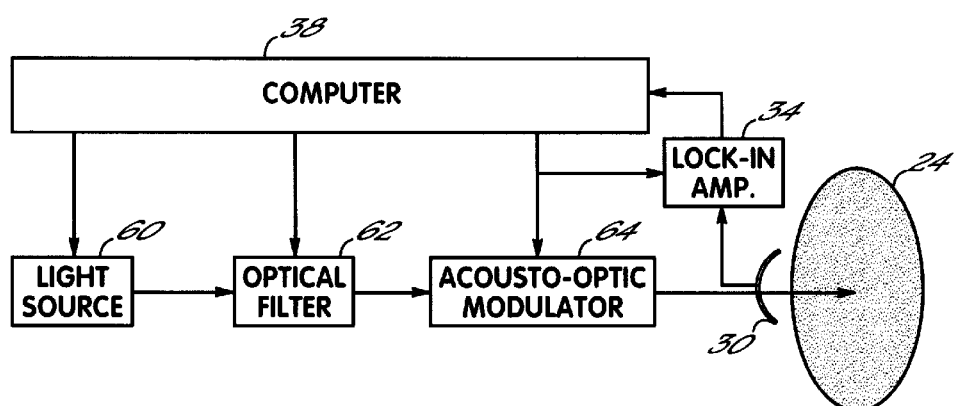
FIG. 4 illustrates a second alternative embodiment of an apparatus for coupling stimulating radiation to tissue and collecting acoustic signals therefrom.

FIG. 4 illustrates a variation on the implementation illustrated in FIG. 3. In this embodiment the transducer 30 has a narrow aperture through which the light beam is allowed to pass. In this embodiment, the light could also be delivered via a fiber optic cable that passes through the transducer.

Figure 5:
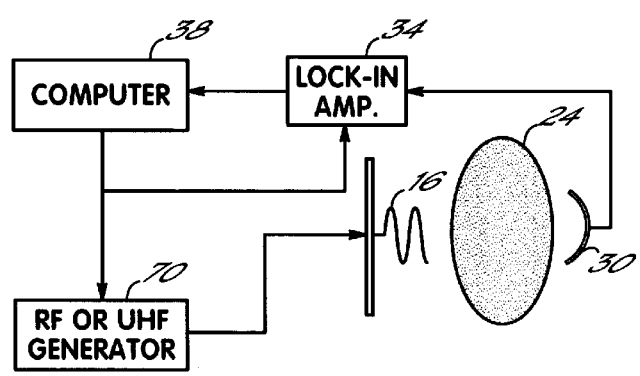
FIG. 5 illustrates a third alternative embodiment of an apparatus for coupling stimulating radiation to tissue and collecting acoustic signals therefrom.

FIG. 5 shows an embodiment where the light source has been replaced by an RF or UHF generator 70. Some of the properties of this generator are that its operating frequency can be adjusted electronically and its output can be modulated internally. Both functions are controlled by a computer 38. Energy is delivered to the tissue with an antenna, such as a metallic hemisphere with a helical coil 16. Such devices are commonly used in the treatment of hyperthermia.

Figure 6:
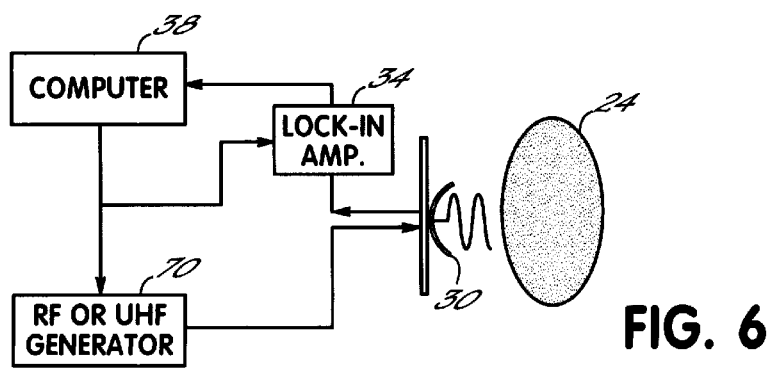
FIG. 6 illustrates a fourth alternative embodiment of an apparatus for coupling stimulating radiation to tissue and collecting acoustic signals therefrom.

In the embodiment of FIG. 6, the transducer 30 and the RF/UHF antenna have been integrated into a single device. The cable from the RF/UHF generator 70 passes through a small aperture in the transducer 30. The front surface of the transducer 30 is used as the ground plane for the antenna.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A method of imaging tissue structures by detecting localized absorption of electromagnetic waves in the tissue, comprising providing a source of electromagnetic radiation in proximity to the tissue;

providing an acoustic sensor which is primarily sensitive to acoustic radiation at a first focal point distant from the sensor;

acoustically coupling the acoustic sensor to the tissue;

irradiating the tissue with continuous, modulating electromagnetic radiation from the source;

detecting resultant pressure waveforms arriving at the acoustic sensor from the first focal point and storing first data representative of the waveforms;

modifying the acoustic sensor to be primarily sensitive to acoustic radiation at a second focal point distant from the sensor;

irradiating the tissue with continuous, modulating electromagnetic radiation from the source;

detecting resultant pressure waveforms arriving at the acoustic sensor from the second focal point and storing second data representative of the waveforms;

combining the first and second data to produce an image of structures in the tissue.

2. The method of claim 1 wherein the electromagnetic radiation is amplitude modulating electromagnetic radiation.

3. The method of claim 1 wherein the acoustic sensor comprises a plurality of transducers each detecting acoustic waves and generating therefrom electrical signals, and detecting pressure waveforms from a focal point of the sensor comprises combining the electrical signals from the plurality of transducers.

4. The method of claim 3 wherein the acoustic sensor further comprises a programmable delay circuit, and wherein modifying the acoustic sensor to have a second focal point comprises delaying one or more of the electrical signals produced by the transducers prior to combining the electrical signals.

5. The method of claim 1 wherein the continuous modulating electromagnetic radiation is amplitude modulating electromagnetic radiation, the frequency of amplitude modulation being substantially less than the frequency of the electromagnetic radiation.

6. The method of claim 5 wherein detecting resultant pressure waveforms arriving at the acoustic sensor comprises demodulating pressure waveforms arriving at the sensor which are at frequencies similar to the frequency of amplitude modulation.

7. The method of claim 6 wherein pressure waveforms arriving at the sensor are demodulated by mixing the pressure waveforms with the frequency of amplitude modulation, and low-pass filtering the result.

8. The method of claim 6 wherein the mixing is performed in phase with frequency components of the waveforms arriving at the acoustic sensor which are at frequencies similar to the frequency of amplitude modulation.

9. The method of claim 1 wherein the continuous modulating electromagnetic radiation is visible light radiation.

10. The method of claim 1 wherein the continuous modulating electromagnetic radiation is infrared light.

11. The method of claim 1 wherein the continuous modulating electromagnetic radiation is radio frequency electromagnetic radiation.

12. A method of characterizing tissue by detecting localized absorption of electromagnetic waves in the tissue, comprising providing a source of electromagnetic radiation in proximity to the tissue;

providing an acoustic sensor which is primarily sensitive to acoustic radiation at a focal point distant from the sensor;

acoustically coupling the acoustic sensor to the tissue;

irradiating the tissue at said focal point and at points where said acoustic sensor is substantially insensitive to acoustic radiation, with continuous, frequency modulating electromagnetic radiation from the source;

detecting resultant pressure waveforms arriving at the acoustic sensor from the focal point during frequency modulation of the electromagnetic radiation;

comparing a frequency of the electromagnetic radiation to the detected resultant pressure waveforms generated at the frequency, to form a measure of absorptivity spectrum of tissue located proximate to the focal point of the acoustic sensor.

13. The method of claim 12 wherein the electromagnetic radiation is amplitude modulating electromagnetic radiation.

14. The method of claim 12 wherein the acoustic sensor comprises a plurality of transducers each detecting acoustic waves and generating therefrom electrical signals, and detecting pressure waveforms from a focal point of the sensor comprises combining the electrical signals from the plurality of transducers.

15. The method of claim 14 wherein the acoustic sensor further comprises a programmable delay circuit, and further comprising modifying the acoustic sensor to have a second focal point by delaying one or more of the electrical signals produced by the transducers prior to combining the electrical signals, and then comparing a frequency of the electromagnetic radiation to the detected resultant pressure waveforms generated at the frequency, to form a measure of absorptivity spectrum of tissue located proximate to the second focal point.

16. The method of claim 12 wherein the continuous modulating electromagnetic radiation is amplitude modulating electromagnetic radiation, the frequency of amplitude modulation being substantially less than frequencies in the frequency modulation range of the electromagnetic radiation.

17. The method of claim 16 wherein detecting resultant pressure waveforms arriving at the acoustic sensor comprises demodulating pressure waveforms arriving at the sensor which are at frequencies similar to the frequency of amplitude modulation.

18. The method of claim 17 wherein pressure waveforms arriving at the sensor are demodulated by mixing the pressure waveforms with the frequency of amplitude modulation, and low-pass filtering the result.

19. The method of claim 17 wherein the mixing is performed in phase with frequency components of the waveforms arriving at the acoustic sensor which are at frequencies similar to the frequency of amplitude modulation.

20. The method of claim 12 wherein the continuous modulating electromagnetic radiation is visible light radiation.

21. The method of claim 12 wherein the continuous modulating electromagnetic radiation is infrared light.

22. The method of claim 12 wherein the continuous modulating electromagnetic radiation is radio frequency electromagnetic radiation.

23. Apparatus for imaging tissue structures by detecting localized absorption of electromagnetic waves in the tissue, comprising a source of electromagnetic radiation in proximity to the tissue;

an acoustic sensor which is primarily sensitive to acoustic radiation at a focal point distant from the sensor, the focal point being modifiable;

a coupling medium acoustically coupling the acoustic sensor to the tissue;

a control circuit connected to the electromagnetic radiation source and acoustic sensor, the control circuit controlling the electromagnetic radiation source to irradiate the tissue with continuous, modulating electromagnetic radiation, and controlling the acoustic sensor to detect resultant pressure waveforms arriving at the acoustic sensor from a first focal point and from a second focal point, and combining pressure waveforms from the first and second focal points to produce an image of structures in the tissue.

24. The apparatus of claim 23 wherein the source of electromagnetic radiation produces amplitude modulating electromagnetic radiation.

25. The apparatus of claim 23 wherein the acoustic sensor comprises a plurality of transducers each receiving acoustic waves and generating therefrom electrical signals, and the control circuit detects pressure waveforms from a focal point of the sensor by combining the electrical signals from the plurality of transducers.

26. The apparatus of claim 25 wherein the acoustic sensor further comprises a programmable delay circuit, and wherein the focal point of the acoustic sensor is modified by delaying one or more of the electrical signals produced by the transducers prior to combining the electrical signals.

27. The apparatus of claim 23 wherein the source of electromagnetic radiation produces amplitude modulating electromagnetic radiation, the frequency of amplitude modulation being substantially less than the frequency of the electromagnetic radiation.

28. The apparatus of claim 27 wherein the control circuit detects pressure waveforms arriving from the focal point of the acoustic sensor by demodulating pressure waveforms arriving at the sensor which are at frequencies similar to the frequency of amplitude modulation.

29. The apparatus of claim 28 wherein the control circuit demodulates pressure waveforms arriving at the sensor by mixing the pressure waveforms with the frequency of amplitude modulation, and low-pass filtering the result.

30. The apparatus of claim 28 wherein the mixing is performed in phase with frequency components of the waveforms arriving at the acoustic sensor which are at frequencies similar to the frequency of amplitude modulation.

31. The apparatus of claim 23 wherein the source of electromagnetic radiation produces visible light radiation.

32. The apparatus of claim 23 wherein the source of electromagnetic radiation produces infrared light.

33. The apparatus of claim 23 wherein the source of electromagnetic radiation produces radio frequency electromagnetic radiation.

34. Apparatus for characterizing tissue by detecting localized absorption of electromagnetic waves in the tissue, comprising a source of electromagnetic radiation in proximity to the tissue;

an acoustic sensor which is primarily sensitive to acoustic radiation at a focal point distant from the sensor;

a coupling medium acoustically coupling the acoustic sensor to the tissue;

a control circuit connected to the electromagnetic radiation source and acoustic sensor, the control circuit controlling the electromagnetic radiation source to irradiate the tissue at said focal point and at points where said acoustic sensor is substantially insensitive to acoustic radiation, with continuous, frequency modulating electromagnetic radiation from the source, detect resultant pressure waveforms arriving at the acoustic sensor from the focal point during frequency modulation of the electromagnetic radiation, and compare a frequency of the electromagnetic radiation to the detected resultant pressure waveforms generated at the frequency, to form a measure of absorptivity spectrum of tissue located proximate to the focal point of the acoustic sensor.

35. The apparatus of claim 34 wherein the source of electromagnetic radiation produces amplitude modulating electromagnetic radiation.

36. The apparatus of claim 34 wherein the acoustic sensor comprises a plurality of transducers each detecting acoustic waves and generating therefrom electrical signals, and the control circuit detects pressure waveforms from a focal point of the sensor by combining the electrical signals from the plurality of transducers.

37. The apparatus of claim 36 wherein the acoustic sensor further comprises a programmable delay circuit, such that the acoustic sensor may modify its focal point by delaying one or more of the electrical signals produced by the transducers prior to combining the electrical signals.

38. The apparatus of claim 37 wherein the control circuit controls the acoustic sensor to have a second focal point, and then compares a frequency of the electromagnetic radiation to the detected resultant pressure waveforms generated from the second focal point at the frequency, to form a measure of absorptivity spectrum of tissue located proximate to the second focal point.

39. The apparatus of claim 34 wherein the source of electromagnetic radiation produces amplitude modulating electromagnetic radiation, the frequency of amplitude modulation being substantially less than frequencies in the frequency modulation range of the electromagnetic radiation.

40. The apparatus of claim 39 wherein the control circuit detects resultant pressure waveforms arriving at the acoustic sensor by demodulating pressure waveforms arriving at the sensor which are at frequencies similar to the frequency of amplitude modulation.

41. The apparatus of claim 40 wherein the control circuit demodulates pressure waveforms arriving at the sensor by mixing the pressure waveforms with the frequency of amplitude modulation, and low-pass filtering the result.

42. The apparatus of claim 40 wherein the mixing is performed in phase with frequency components of the waveforms arriving at the acoustic sensor which are at frequencies similar to the frequency of amplitude modulation.

43. The apparatus of claim 34 wherein the source of electromagnetic radiation produces visible light radiation.

44. The apparatus of claim 34 wherein the source of electromagnetic radiation produces infrared light.

45. The apparatus of claim 34 wherein the source of electromagnetic radiation produces radio frequency electromagnetic radiation.

* * * * *